United States Patent
Holtzapple et al.

[11] Patent Number: 5,962,307
[45] Date of Patent: *Oct. 5, 1999

[54] APPARATUS FOR PRODUCING ORGANIC ACIDS

[75] Inventors: Mark Holtzapple, College Station; Richard Davison, Bryan, both of Tex.; Mitch Loescher, San Francisco, Calif.; Michael K. Ross, College Station, Tex.

[73] Assignee: The Texas A&M University System, College Station, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/956,469

[22] Filed: Oct. 23, 1997

Related U.S. Application Data

[62] Division of application No. 08/688,051, Jul. 31, 1996, Pat. No. 5,874,263.

[51] Int. Cl.⁶ ................................................. C12M 1/113
[52] U.S. Cl. ................................. 435/294.1; 435/290.4; 435/300.1; 435/813; 435/819
[58] Field of Search ................................. 435/139, 140, 435/141, 289.1, 290.4, 294.1, 300.1, 801, 813, 819; 71/10

[56] References Cited

U.S. PATENT DOCUMENTS

| | | |
|---|---|---|
| 2,458,431 | 1/1949 | Schlenz . |
| 3,067,107 | 12/1962 | Wayman et al. . |
| 3,241,943 | 3/1966 | Bystrom . |
| 3,933,628 | 1/1976 | Varani . |
| 4,022,665 | 5/1977 | Ghosh et al. ........................... 435/167 |
| 4,057,401 | 11/1977 | Boblitz ................................. 435/294.1 |
| 4,100,023 | 7/1978 | McDonald . |
| 4,252,901 | 2/1981 | Fischer et al. ....................... 435/294.1 |
| 4,267,049 | 5/1981 | Erickson et al. ........................ 210/606 |
| 4,318,993 | 3/1982 | Ghosh et al. . |
| 4,405,717 | 9/1983 | Urbas ..................................... 435/140 |
| 4,444,881 | 4/1984 | Urbas ..................................... 435/139 |
| 4,536,584 | 8/1985 | Eskamani et al. ....................... 549/429 |
| 4,612,286 | 9/1986 | Sherman et al. ........................ 435/157 |
| 4,636,467 | 1/1987 | Chynoweth . |
| 4,665,027 | 5/1987 | Dale et al. .............................. 435/162 |
| 4,814,273 | 3/1989 | Brumm et al. . |
| 4,935,360 | 6/1990 | Klemps et al. . |
| 5,053,142 | 10/1991 | Sorensen et al. ....................... 210/742 |
| 5,125,977 | 6/1992 | Grohmann et al. ....................... 127/36 |
| 5,254,465 | 10/1993 | Wise ...................................... 435/140 |
| 5,370,801 | 12/1994 | Sorenson et al. ....................... 210/742 |
| 5,412,126 | 5/1995 | King et al. .............................. 554/185 |
| 5,464,760 | 11/1995 | Tsai et al. ............................... 435/139 |
| 5,506,123 | 4/1996 | Chieffalo et al. ....................... 435/139 |
| 5,510,526 | 4/1996 | Baniel et al. ........................... 562/580 |

FOREIGN PATENT DOCUMENTS

| | | |
|---|---|---|
| 0152730 | 8/1985 | European Pat. Off. . |
| 60-102998 | 6/1985 | Japan ................................. 435/294.1 |
| 8001516 | 9/1993 | Sweden . |
| 1028822 | 5/1966 | United Kingdom . |
| 2013170 | 8/1979 | United Kingdom . |
| 2125064 | 2/1984 | United Kingdom . |

*Primary Examiner*—William H. Beisner
*Attorney, Agent, or Firm*—Baker & Botts LLP

[57] ABSTRACT

A continuous process and apparatus for preparing organic acids and their salts from biomass. Biomass flows from a region of fresh biomass and high acid and acid salt concentration to a region of digested biomass and low acid and acid salt concentration in a fermentation apparatus under anaerobic conditions. Organic acids and acid salts produced by the process of the present invention are volatile fatty acids such as acetic, butyric and propionic acids and their salts such as calcium acetate, calcium propionate, and calcium butyrate. The apparatus of the present invention contains at least two fermentation reactors in series to increase the biomass residence time in the reactors. The fermentation reactors of the present invention are imbedded in the ground with earthen berms as support for sides having three layers. The core of the reactors are covered with a flexible covering to maintain an anaerobic environment.

9 Claims, 3 Drawing Sheets

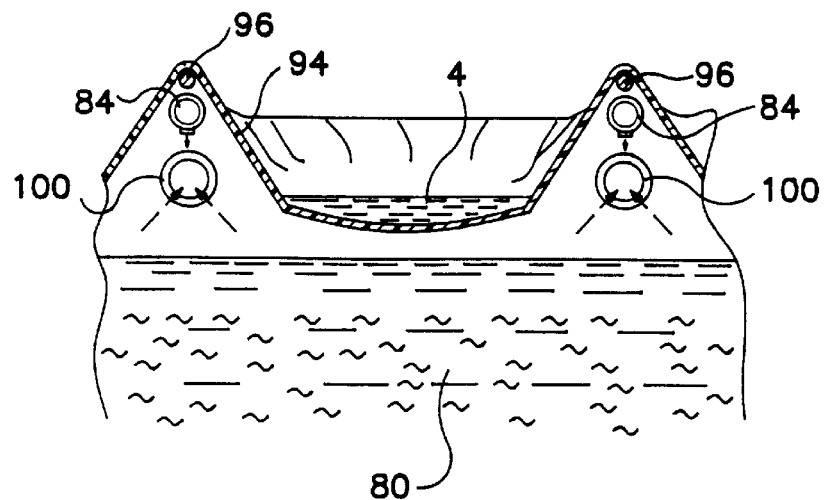
FIG. 3
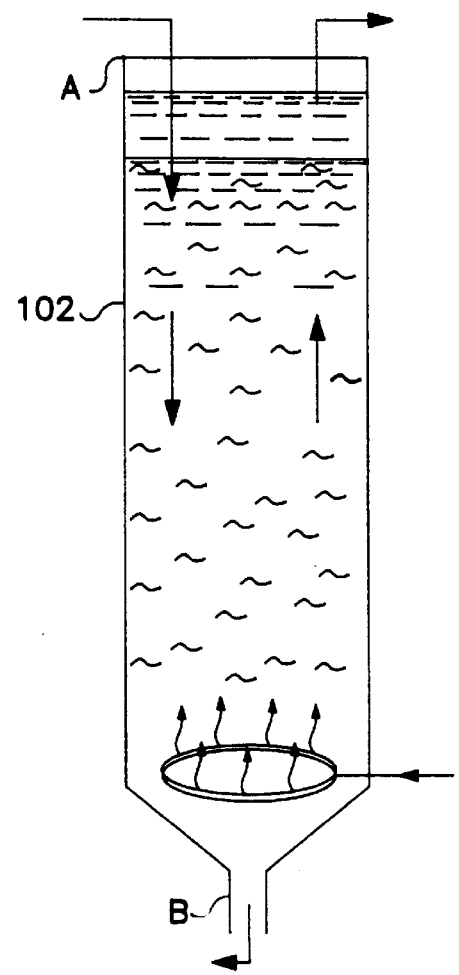
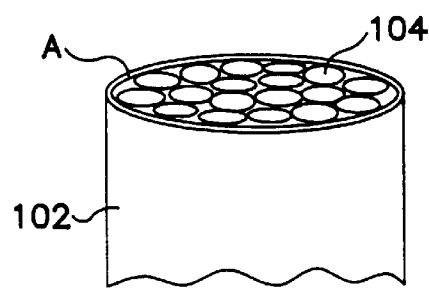
FIG. 5    FIG. 4

APPARATUS FOR PRODUCING ORGANIC ACIDS

This application is a divisional of Application Ser. No. 08/688,051, filed Jul. 31, 1996, entitled METHOD AND APPARATUS FOR PRODUCING ORGANIC ACIDS, now U.S. Pat. No. 5,874,263.

BACKGROUND OF THE INVENTION

The present invention is directed to a method and apparatus for producing organic acids. More specifically, the present invention is directed to a method and apparatus for producing organic acids from biomass.

Organic acids are important chemicals of commerce. Historically, organic acids were produced from animal fat or vegetable oil sources or from petroleum sources in substantially nonaqueous systems. More recently, organic acids have been identified as among the most attractive products for manufacture from biomass by fermentation. Biomass can be defined as any animal or plant-based material of carbohydrate, protein or fat composition. Among the readily available sources of biomass are municipal solid waste (MSW) and sewage sludge (SS). At present, great expenditures of public funds are used to dispose of such wastes, including costs involved in treatment, transport, incineration or dumping in landfills or oceans of such material. The recovery of valuable products from biomass such as MSW and SS could recover the costs of disposal as well as reduce reliance on nonrenewable fossil fuel resources which serve as feedstock for most industrial organic acid production. Fermentation, therefore, can convert renewable organic materials now considered a costly waste into valuable chemical commodities.

During fermentation, the acids are produced by the microorganisms in dilute aqueous solutions such that recovery of the acids in pure form involves separation from a large quantity of water. Thus, to reduce separation costs, it is desirable to produce the acids at high concentrations. However, at high acid concentrations the fermentation is inhibited which limits the ultimate conversion of the biomass. The acids soon lower the pH of the fermentation medium to a point at which the microorganisms no longer grow or are active. To continue fermentation, the system is purged of acid or the pH is raised by adding neutralizing agents such as ammonia, sodium bicarbonate, calcium hydroxide or calcium carbonate. Addition of neutralizing agents form salts of the acids such as calcium acetate which are substantially less inhibitory than the acids themselves. Nonetheless, these neutralized salts are inhibitory and, at high concentrations, they will also limit the extent of biomass digestion. Accordingly, the need to provide high acid concentration to reduce the cost of product separation is incompatible with the need for maintaining high levels of digestion. Thus there is a need for a method and apparatus for improving the efficiency of producing organic acids from biomass.

Accordingly, a primary objective of the present invention is to provide for a novel and improved method of producing organic acids from biomass by fermentation.

Another objective is to provide for an improved method of producing organic acids by the fermentation of biomass and maintain high biomass digestion and high product concentrations to reduce product recovery costs.

A further objective is to provide for a novel apparatus for converting biomass to organic acids and maintain high biomass digestion rates and high acid concentrations to reduce acid recovery costs.

Still yet an additional objective of the present invention is to provide for an improved reactor for performing fermentation of biomass.

Additional objects, advantages and novel features of the present invention will be set forth in part in the description and claims which follow, and in part will become apparent to those skilled in the art upon examination of the following or can be learned by practicing of the invention.

SUMMARY OF THE INVENTION

The present invention is directed to a novel and improved method and apparatus for producing organic acids from biomass by means of a continuous anaerobic heterogeneous fermentation process.

Unfortunately, the production of organic acids from biomass is much less efficient than is desirable in the industry and as yet has not met the potential of cost savings with respect to reducing municipal and industrial organic waste disposal costs or for providing an alternative to fossil fuel feedstocks. An important reason that fermentation of biomass has not yet met its potential has been discussed above. Thus, as the fermentation process proceeds and the fermentation environment becomes inhibitory from the high concentration of organic acids and their salts, bacterial growth is reduced thus reducing biomass digestion. Minimizing product concentration on the other hand greatly increases the costs of recovering the product. Thus, the incompatibility of high biomass digestion and high product concentration for ease of recovery has not been overcome until now.

The process and apparatus of the present invention can be characterized as providing for a continuous countercurrent heterogeneous fermentation of biomass and recovery of organic acids and their salts as product. The continuous countercurrent method of the present invention overcomes the incapability of high digestion and high product concentration which occurs in conventional batch or current continuous reactor systems. In the continuous countercurrent method of the present invention, biomass flows from a region of fresh biomass and high product concentration to a region of digested biomass and low product concentration while an aqueous product extractant stream flows from a region of digested biomass and low product concentration to a region of fresh biomass and high product concentration from which a highly concentrated acid stream is recovered. Thus, a multistage process is used, wherein the stage which is provided with the most digested biomass is maintained with the lowest product concentration by the addition of fresh water, while the stage with the highest concentration of product is provided with fresh biomass and the product is recovered. Advantageously, the countercurrent fermentation system provides in each stage an environment favorable for the anaerobic fermentation bacteria such that the optimum digestion of the biomass and production of organic acids and their salts is maintained, and, importantly, recovery of same is provided at the stage of highest product concentration. The product which is formed and recovered in accordance with this invention includes, but is not limited to, the volatile fatty acids acetic acid, propionic acid, butyric acid and their salts.

The apparatus employed to practice the continuous countercurrent heterogeneous fermentation process of the present invention includes at least two fermentation reactors, but can include three or more reactors. Fresh biomass is directed to the first reactor and conveying means are provided to transfer the partially digested biomass from the first reactor to the second reactor for further digestion. Further digestion of the biomass can take place in subsequent reactors, if desired, wherein conveying means are provided between each successive pair of reactors. Means to direct an aqueous product-extractant stream countercurrent to the flow of biomass is provided to control product concentration in each of the reactors and maintain an environment in each reactor which is conducive to anaerobic digestion. Thus, in the last reactor of the chain, that being the reactor containing the most digested biomass, a fresh water stream is provided to reduce product concentration. Piping is provided to direct the product-containing stream from the last reactor to the next reactor which will now be provided with an increased product concentration. Piping means are also provided to direct the more concentrated product-containing aqueous stream to the first reactor in the chain which contains the fresh biomass. The highly concentrated product-containing stream from the first reactor can then be treated to recover the product. The aqueous stream can be mixed or contacted with the biomass in each reactor or with the biomass outside the reactor to extract the product therefrom. Several extracting systems are provided by this invention.

For large-scale fermentations, each reactor of the apparatus is buried in the ground with a berm of soil surrounding the reactor for support. The core of the reactor is lined with a water barrier onto which a porous material is layered. An abrasion-resistant liner is placed on the top of the porous material. The angle of the porous material is the natural angle resulting when the porous material is piled. This natural angle prevents stresses against the liner because the liner need not support the weight of the porous material.

The roof of the reactor consists of a flexible membrane to allow for expansion when fermentation gases are formed during the synthesis of organic acids and their salts. To remove gases such as hydrogen, carbon dioxide, and methane, gas collection manifolds are placed in the berm and penetrate the sides of the reactor. Feed pipes also are provided for transporting biomass into the reactor and withdrawal pipes for removing digested biomass from the reactor. Means are provided to treat the digested biomass to recover the product produced during fermentation and piping provided to direct the biomass to at least one successive reactor in the chain of the countercurrent system of this invention. Recycle of the biomass in the reactor is provided in addition to product recovery to uniformly mix the fermenting materials in each reactor and to provide a longer solids residence time for additional biomass digestion.

Advantageously, the process and apparatus of the present invention provide for increased yields of organic acids and salts thereof compared to conventional continuous reactor systems because of reduced exposure of anaerobic bacteria to high product concentrations.

BRIEF DESCRIPTION OF THE DRAWINGS

FIG. 3 is an illustration of a transverse sectional view of the upper portion of the fermentation reactor of FIG. 2 taken along line 3—3.

FIG. 4 is an illustration of a countercurrent product extraction column of the present invention.

FIG. 5 is an illustration of the countercurrent product extraction column of FIG. 4 showing baffles in the column.

DETAILED DESCRIPTION OF THE INVENTION

Figure 1:
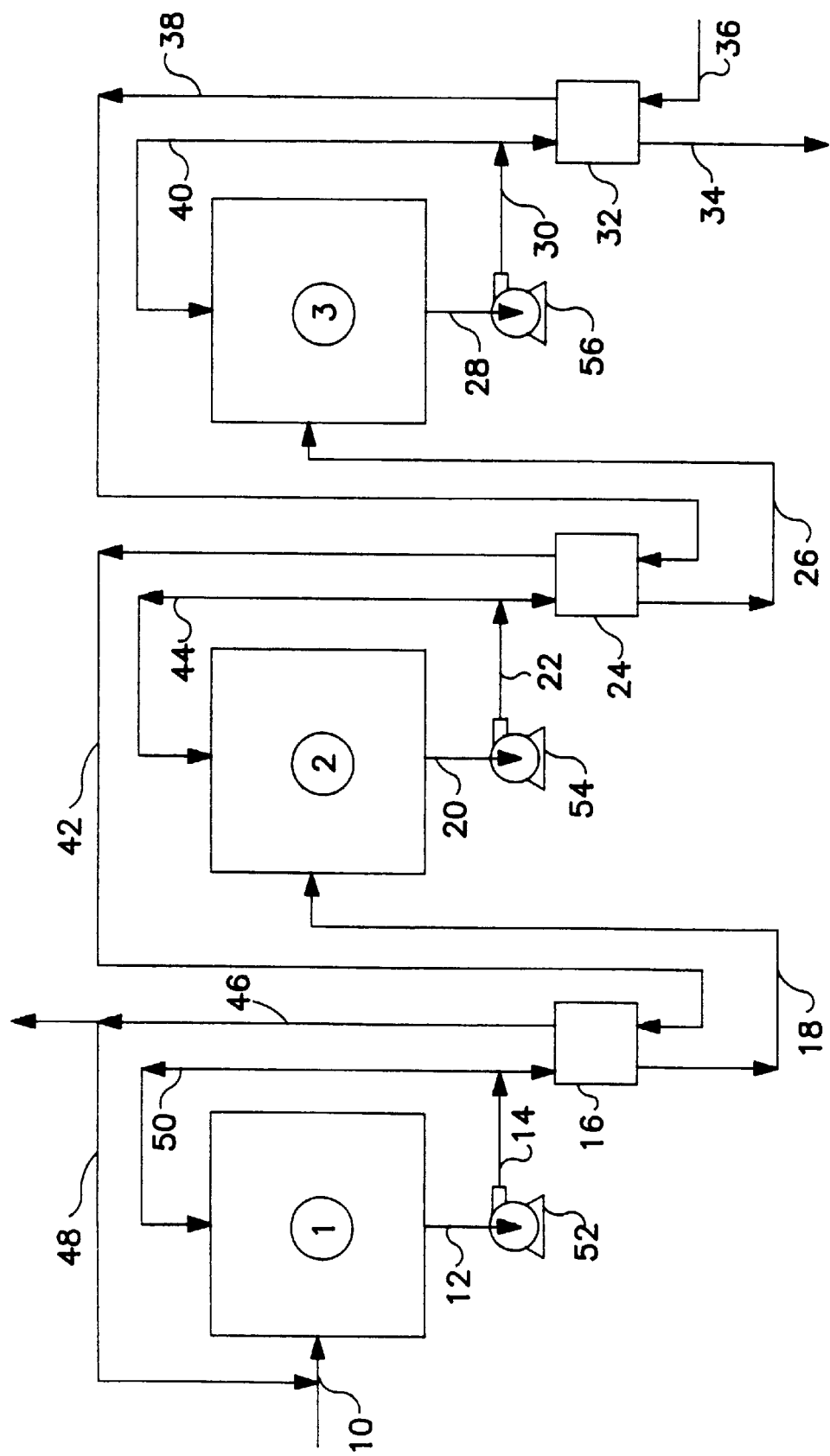
FIG. 1 is a schematic representation of the continuous countercurrent heterogeneous fermentation system of the present invention.

The present invention is directed to a continuous countercurrent heterogeneous fermentation process and apparatus for the production of organic acids and their salts from biomass. The organic acids produced by the process of the present invention include many different types of organic acids such as aliphatic carboxylic acids of 2–6 carbons such as acetic acid, propionic acid, butyric acid, iso-butyric acid, iso-valeric acid, n-valeric acid, caproic acid and the like as well as their salts. The method of the present invention can digest over 60 wt. % of biomass introduced into the fermentation system with about 70 wt. % of the digested biomass converted to organic acids and their salts.

Biomass used to produce organic acids and their salts by the fermentation process of the present invention includes any organic material such as plant or animal matter containing proteins, fats and/or carbohydrates. Examples of such biomass include, but are not limited to, manure, lignocellulose which contains lignin, hemicellulose, and cellulose or any such plant materials, municipal solid waste, sewage and the like.

In general, the biomass, preferably in the form of an aqueous slurry, is introduced into a fermentation reactor provided with an anaerobic environment. Upon fermentation or digestion of the biomass, organic acids and their salts are produced. The pH of the biomass slurry can eventually drop to about 4.8 where the fermentation process ceases almost completely as such an environment is too acidic to sustain effective anaerobic bacterial fermentation. Thus, a neutralizing agent can be added to the system to maintain a pH above about 4.8 in each reactor. Suitable neutralizing agents include ammonium, sodium, potassium and calcium salts of hydroxides, carbonates and bicarbonates. Preferably, calcium carbonate is employed to maintain the desirable pH range of the system. The neutralizing agent can be added to the system at any point where it is needed to maintain the pH range. Preferably, the buffer is added with the fresh biomass entering the fermentation process.

Because the pH range of the fermentation process of the present invention is within about 4.8 to below 7.0, the product of the fermentation process is a mixture of free acids and their salts. For example, at about pH 4.8 the product contains about 50 wt. % each of the free acid species and salts of the acids. At a pH of about 5.8, there is about 10 wt. % acid and about 90 wt. % salt, and at a pH of about 6.8 there is about 1.0 wt. % acid and about 99 wt. % salt.

A pH below about 5.8 effectively suppresses the formation of unwanted methanogen formation. If the fermentor is operated above a pH of 5.8, methanogen inhibitors may be added to the process to inhibit methanogen formation. Methanogen inhibitors can be added to the fermentation reactors, or, preferably, the methanogen inhibitors can be added to the fresh liquid stream. Acetic acid, a desirable product of the process of the present invention, is an intermediate in the conversion of biomass to methane and carbon dioxide. Accordingly, it is desirable to prevent fermentation of the acids to gaseous products to insure a high yield of the acid product. Methanogen inhibitors such as 2-bromoethanesulfonic acid, monensin and pyromellitic diimide can be employed to prevent methane formation during the process of the present invention. Preferably, about a 0.001 M solution of 2-bromoethanesulfonic acid is employed.

To further counter the inhibitory effect of the high product concentrations on the anaerobic bacteria, the biomass is passed through a countercurrent system where the digested biomass is washed with a liquid, such as water, to remove products to provide an environment more favorable to bacterial growth and fermentation in a second fermentation reactor. A portion of the digested biomass can be recycled to the first fermentation reactor before being sent to the second fermentation reactor. Advantageously, the recycling of a fraction of the biomass back to the first fermentation reactor provides for a longer solids or biomass residence time in the fermentation reactors to increase digestion and provide more uniformity of the reaction medium in the reactor. Preferably, the countercurrent water stream used to extract the products from the biomass is contacted with the biomass between reactors to reduce liquid residence time in the reactor. The lower liquid residence time allows a high solids concentration and high production rates and recovery of a highly concentrated product stream. Thus the amount of time in which the biomass is exposed to high product concentrations is reduced providing for high digestion of biomass. Biomass residence times range from about 20 to about 90 days, preferably, about 30 to about 60 days in the fermentation process. Liquid residence time ranges from about 5 to about 30 days, preferably, about 9 to about 18 days.

FIG. 1 is a schematic of the continuous countercurrent heterogeneous fermentation process of the present invention. Initially, fresh biomass is fed via line 10 into the first reactor 1 of a chain of reactors, which as shown also includes reactors 2 and 3. As the biomass flows from reactors 1 to 3, the biomass is increasingly digested. Liquid such as fresh water is fed via line 36 into the reactor 3 system which contains the most digested biomass to extract the products contained therein. Accordingly, the most digested fermentation medium is provided with the lowest product concentration. The aqueous, product extractant stream passes countercurrently to the flow of biomass from reactor 3 to reactors 2 and 1 subsequently increasing the product concentration of the biomass in each reactor system. Thus, although the system of reactor 1 contains the highest product concentration, it also contains the freshest nondigested biomass. Accordingly, in each of the reactors 1, 2 and 3, the product concentration is controlled to maintain fermentation. The highly concentrated product stream leaves the reactor 3 system via line 46. The biomass leaving each reactor 1, 2 and 3 is contacted by the aqueous, product-extractant stream preferably between reactors in a product extraction apparatus depicted at 16, 24 and 32, respectively. Although FIG. 1 illustrates three fermentation reactors, the number of reactors can range from two or more reactors in series. Preferably four to six reactors in series are used to achieve optimum organic acid synthesis. As the number of reactors in series increases in the countercurrent fermentation system, the residence time of the biomass to obtain a given amount of product and digest a given amount of biomass decreases. For example, a countercurrent fermentation system having four reactors or stages in series can produce about the same amount of product and digest about the same amount of biomass over about a 30 hour biomass residence time as a two reactor fermentation system can in about a 45 hour biomass residence time.

More specifically, again referring to FIG. 1, biomass is fed into reactor 1 by means of line 10 which can be any suitable feed system employed in the industry. After a suitable residence time, the biomass flows out of reactor 1 through line 12 where it is pumped by pump 52 through line 14 into the product extraction system 16 where the partially digested biomass is washed with an aqueous, product extractant stream flowing via line 42 countercurrent to the biomass to remove product from the biomass. Although a countercurrent product extraction process is disclosed, any useful process can be employed to remove the products from the biomass. Several schemes are disclosed below. The water stream originates at the opposite end of the system to that of the fresh biomass feed through line 36 and contains product extracted from biomass exiting reactors 2 and 3. The aqueous wash containing the product passes from the product extraction system 16 through line 46 and represents a stream containing about 2.0–4.5 wt. % (about 20.0 gm/L–45.0 gm/L) product in water. The product is separated from the water by a suitable separation means (not shown). The product concentration in the aqueous stream is sufficiently high to provide economical separation and recovery of product. A fraction of the aqueous stream can be recycled to the system by line 48 to provide the biomass feed in reactor 1 in the form of a slurry.

Prior to the biomass passing into the product extraction system 16, any desirable fraction of the biomass can be recycled to reactor 1 by means of line 50 for an additional residence time where the recycled fraction of biomass undergoes further digestion.

The digested biomass leaving the product extraction system 16 is directed to reactor 2 by means of line 18 where the biomass undergoes further digestion in an environment with lower product concentration than that found in reactor 1 to produce additional product. The further digested biomass flows from reactor 2 through line 20 where it is pumped through line 22 by pump 54 to a second product extraction system 24. A fraction of the further digested biomass from reactor 2 is recycled to reactor 2 by means of line 44 for additional residence time in reactor 2. The fraction of further digested biomass passed into product extraction system 24 undergoes extraction wherein the biomass can again be washed such as with a product-containing aqueous stream flowing in the opposite direction of the biomass to purge the biomass of further organic acids and salts of organic acids. The wash water with the product passes through line 42 to product extraction system 16 and then through line 46 where the product is collected and eventually separated and recovered from the aqueous phase.

The additional digested biomass passes from product extraction system 24 into reactor 3 by means of line 26 for additional digestion and solids residence time to produce additional amounts of product. The digested and spent biomass is directed from reactor 3, after a suitable residence time, into line 28 where it is pumped through line 30 by pump 56 into a final product extraction system 32. Again, a fraction of the biomass can be recycled to reactor 3 via line 40 for further residence time in reactor 3. The remaining fraction of biomass passes into product extraction system 32 where it is washed with fresh water flowing from line 36 to remove any product. The water washes the biomass of most of the acids and acid salts and then passes from product extraction system 32 through line 38 to product extraction system 24 to recover additional acid product from the biomass and concentrate the aqueous stream with product for eventual recovery. The spent biomass passes from product extraction system 32 through line 34.

Prior to removing the spent biomass from the system, the spent biomass slurry is passed through a filtering system (not shown) where anaerobic microorganisms in the biomass are separated from the biomass and returned (not shown) to the countercurrent fermentation system. Any suitable filtration system can be employed to separate the anaerobic microbes from the spent biomass slurry. Preferably, the spent biomass with microbes passes into a centrifuge operated at a low speed of from about 1,000 to about 2,000 rpm to separate the spent biomass from the microbes. The microbes and any wash water from the slurry then pass into a second centrifuge operated at a fast speed of from about 2,500 to about 5,000 rpm to separate the anaerobic microbes from the wash water. The anaerobic microbes are then recycled to reactor 1 by an appropriate means (not shown). Such a procedure allows a high microbe concentration to be maintained in the fermentation reactors.

The process of fermentation generates heat. To eliminate excess heat from the fermentation system, heat exchangers (not shown) can be placed between each reactor to remove heat from liquid streams 38 and 42. Any suitable heat exchanger can be employed.

Figure 2:
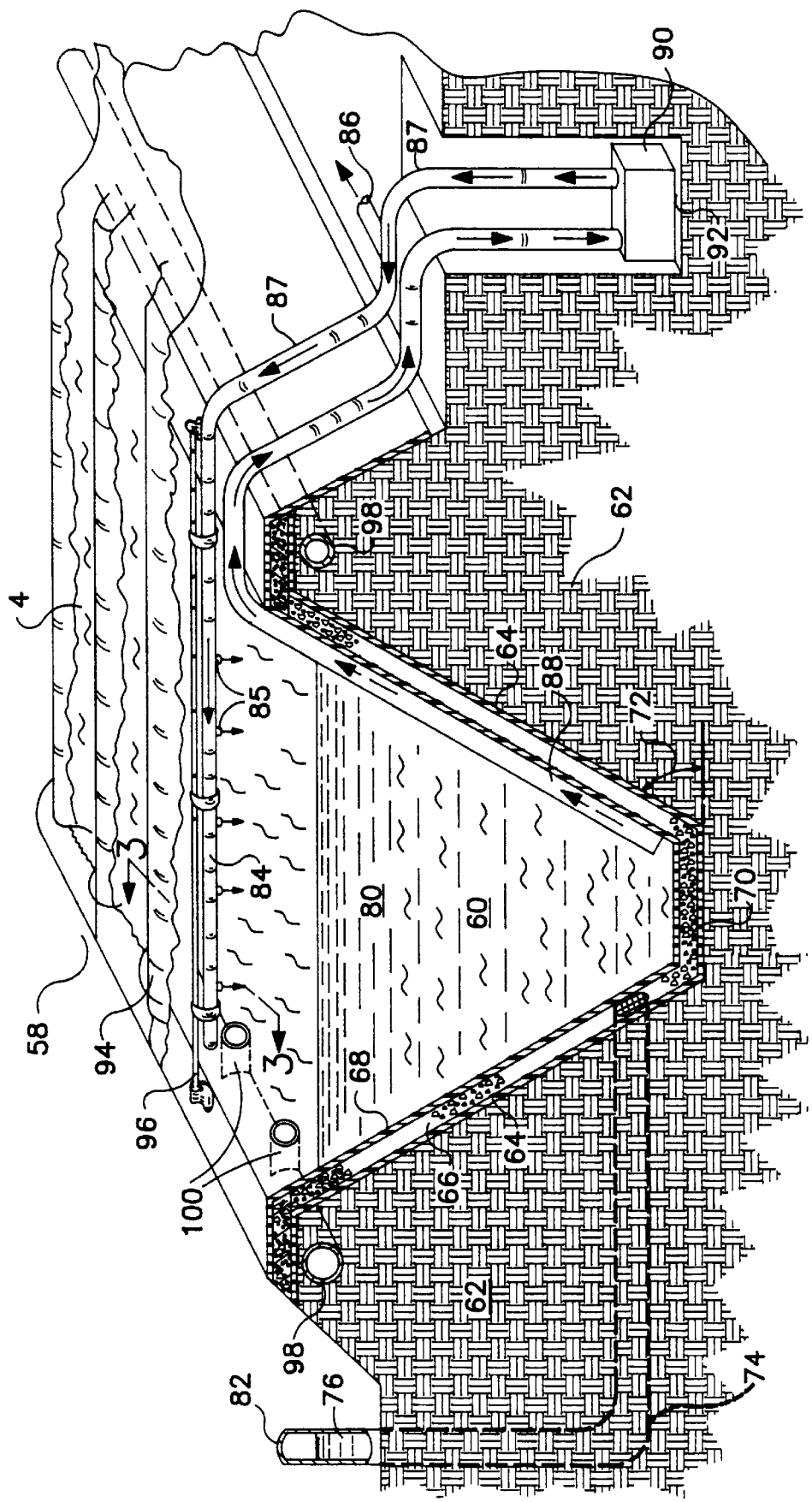
FIG. 2 is an illustration of a cross sectional view of a fermentation reactor of the present invention.

Fermentation reactors of the present invention can include any type of fermentation reactor which can be arranged in a series such that a continuous countercurrent system of anaerobic fermentation can be performed to produce organic acids and their salts and recovery thereof in a concentrated aqueous stream. Preferably, the fermentation reactors of the present invention are in-earth reactors having a means for transporting biomass into the reactor core, uniformly mixing the fermentation medium and providing for removal of the partially digested biomass. FIG. 2 is an illustration of a preferred fermentation reactor within the scope of the present invention.

The fermentation reactor 58 has a core 60 which is a trench dug from the earth with berms 62 as supporting walls composed of the soil dug to make the core. The sides of the core 60 are provided with a water barrier 64 composed of clay, geomembrane, synthetic polymer, asphalt and the like to prevent seepage into the berm supporting walls. A porous layer 66 composed of sand, gravel, plastic beads and the like is placed on top of the water barrier 64 to provide a porous surface. A liner 68 is placed on top of the porous layer 66. The liner 68 can be composed of any suitable material that is abrasion resistant and impermeable to water, such as a rubber material or synthetic polymer material such as polyvinyl chloride (PVC), polyethylene and the like. The floor 70 of the core 60 can be concrete or the same material used for the liner 68. To counteract the fluid pressure inside the reactor, water is placed within the porous layer 66. The angle 72 of the porous layer 66 is the natural angle resulting when the gravel is piled such that there are no stresses against the liner 68.

A standpipe 74 containing water 76 penetrates the bottom of water barrier 64 into the porous layer 66 and extends out of the surface of the ground 78. The acid content of the water in the porous layer 66 can be checked periodically to determine if the liner 68 over the porous surface has ruptured and is leaking out of the reactor core 60. To balance pressure across liner 68, the liquid level in standpipe 74 equals the liquid level of the core 60.

Biomass is fed and recycled into reactor 58 by means of distributor pipe 84 placed across the top surface of biomass 80 and which contains a plurality of holes 85 to direct the biomass into the interior of core 60. To insure even distribution of the biomass slurry into core 60, either distributor pipe 84 extends across the whole top surface of reactor 58 or a plurality of distributor pipes 84 can be provided feed via a single or plurality of pumps 90.

Biomass and organic acids and acid salts products are removed from the core 60 of reactor 58 by means of exit pipe 88 which opens at the bottom of core 60. Again, it is preferred to provide a plurality of exit pipes 88 spaced throughout core 60. One or more pumps 90 are employed to assist in moving biomass into and out of the reactor core 60. Any type of pump suitable for moving a slurry or suspension can be employed. Preferably, the pump is arranged such that it rests in a pump well 92 at the same level as the bottom of the reactor core. This arrangement provides for sufficient head to readily move the biomass slurry from the bottom of core 60 and maintain a uniform fermentation medium in the reactor.

Pump or pumps 90 direct the biomass from reactor core 60 via line 87 for recycle into core 60 via distributor pipe 84 or to a T-connector 86 which directs a fraction of the digested biomass to a product extraction system and eventually on toward another fermentation reactor. A valve (not shown) placed adjacent T-connector 86 can be adjusted to determine the fraction of biomass directed from line 87 to distributor pipe 84 and to the T-connector 86 for extraction of the product.

To maintain an anaerobic environment within the reactor core, a covering such as a tarp 94 is placed over the reactor core 60. The tarp 94 can be made of any type of flexible material such that the tarp can expand when gases are formed during fermentation. As shown in FIGS. 2 and 3, the covering or tarp 94 is supported over the top of the reactor core 60 by cables 96 traversing the reactor and supported to the ground from the top of each berm 62. Water 4 laying on the tarp 94 provides weight to prevent the tarp 94 from flapping in the wind. Gas collection manifolds 98 are provided at either or both ends of the reactor 58 and are situated in the berms 62. Each gas manifold 98 contains a series of gas collection manifold ports 100 which open into core 60 under the tarp 94. The gas collection manifolds 98 collect the gas from the reactor core formed during fermentation by means of the gas collection ports 100. Gases formed during fermentation include hydrogen, carbon dioxide and methane. The amount of methane formed can be significantly reduced by adding methanogen inhibitors to the system or by operating at a low pH, as discussed above.

Alternatively, the reactor of the present invention can have a flexible membrane roof with transverse supporting arches across the core of the reactor (not shown) instead of supporting cables. In addition to supporting the flexible membrane, the supporting arches also can support a feed pipe over the flexible membrane which penetrates the membrane to transport biomass into the reactor. The supporting arches can be composed of any material suitable for supporting the feed pipe such as metal or polymer plastics such as polyvinyl chloride. To ensure that biomass is evenly distributed across the surface of the slurry in the reactor, motorized fans or slingers can be placed in the feed pipes where biomass is emptied into the reactor.

As an alternative to exit pipe 88, biomass slurry can be removed from the reactor by a series of holes on the floor of the reactor leading to exit pipes under the reactor. Tuning rings placed over the holes at the bottom of the reactor ensure that the biomass slurry leaving the reactor leaves evenly. The diameter of the tuning rings can be adjusted to ensure a proper flow rate of biomass slurry from the reactor. Reactors within the scope of the present invention can be of any suitable shape or form. For example, the reactor can be of rectangular shape or it can be an inverted frustrum of a right circular cone and the like.

To recover the products from the biomass, it is preferred to wash the biomass with an aqueous stream between adjacent reactors. Any suitable liquid extraction apparatus can be employed. A preferred system which provides for countercurrent flow between the biomass and aqueous stream is illustrated in FIG. 4. FIG. 4 illustrates a useful product extraction column 102. The digested biomass from the reactor enters column 102 at the top thereof designated as end A and leaves column 102 at bottom end B.

Wash liquid is pumped from bottom end B, contacts and washes product from the oppositely flowing biomass and leaves column 102 at end A as a product-containing aqueous steam. To ensure uniform flow in the countercurrent column and, in particular, to eliminate non-uniform "channeling" of the liquid through the biomass, it may be useful to include baffles within column 102. Accordingly, FIG. 5 shows column 102 containing vertical, tubular baffles 104 which prevent channeling of the wash water and the biomass to improve product recovery.

Another product extraction system which can be used to recover the products from the biomass includes a series of alternating filters and mixers where the biomass is mixed and washed with water, preferably countercurrent to the flow of biomass and the mixture directed to a filter which separates the biomass from the product-containing wash water. The filtered biomass then passes into the next mixer. The number of washings and filterings in the product extraction system can vary. Preferably, the product extraction system employs from two to four washings and filterings. The filter employed can be any suitable filter that can separate biomass from wash water. Examples of such filters include, but are not limited to, filter presses, a centrifuge, rollers or true filters. After the biomass passes through the last filter, it is passed to the next fermentation reactor for an additional solids residence time. Prior to entering the product extraction system, a fraction of the biomass can be recycled to the first reactor for a longer residence time in the first reactor.

An additional product extraction system which can be used to practice the present invention is an upflow extractor. In the upflow extractor, biomass is cyclicly washed of product in a series of containers such that the product in the upstream biomass/product mixtures becomes progressively dilute. The product is serially concentrated downflow from the most dilute biomass and product mixture. The aqueous product layer which separates from the biomass layer after mixing is decanted and passed downflow to an adjacent container where the biomass slurry with a higher product concentration than the biomass of the previous container and the added product are mixed. The container holding the biomass with the highest product concentration is at the end of the wash cycle and is decanted to remove the product. A portion of the decanted concentrated product is removed from the container by means of a product exit line and collected as end product. The container with the biomass of the lowest product concentration is emptied of its contents into a biomass exit line which carries the biomass to a reservoir where the biomass is filtered of any product by a suitable filtration apparatus and directed to a fermentation reactor for further digestion. The number of containers in series is at least two. Preferably, five or more are employed to achieve optimum washing of the biomass and optimum recovery of product.

Another useful product extraction system comprises a diffuser. A diffuser is an apparatus which serves a dual purpose as both a conveyer to transport biomass from one reactor to another and also a filter for removing liquid from the biomass. Within the countercurrent process of this invention, the biomass conveyed downstream on the diffuser is washed with an increasingly dilute aqueous acid stream as the biomass is conveyed from one reactor to another. The biomass slurry on the conveyer belt of the diffuser can comprise about a 1:10 to about 1:8 solid:liquid ratio. Such a high water content allows for the rapid flow of liquid through the biomass since there is no compaction of biomass. The liquid wash which drips through the biomass is collected in a series of tanks. The liquid from one tank is sprayed onto the biomass and collects in an adjacent tank. To minimize the amount of excess liquid along the diffuser belt, a set of rollers can be placed between each adjacent tank to squeeze out the liquid. A final set of rollers at the end of the diffuser before the biomass flows to an adjacent rector establishes the liquid content of the biomass sent to the adjacent reactor. The amount of biomass:liquid ratio ranges from about 1:4 to about 1:6 when entering the adjacent reactor.

The following examples are intended to illustrate the process of the present invention but are not intended to limit the scope of the present invention.

EXAMPLE 1

Six fermentations were performed in individual fermentation reactors to show that high volatile fatty acids and salts concentrations formed during the fermentation process can cause inhibition of microbial digestion of biomass.

The biomass employed was ground rye grass obtained from the Agricultural Engineering Research Laboratory at Texas A&M University. The inoculum was obtained from cow rumen. Quantitative acid hydrolysis was performed on the untreated rye grass. The lignin and ash content of the rye grass were determined to be about 17.5 wt. %. The ground rye grass was pretreated with a 0.1 gm calcium hydroxide/gm of biomass to make digestion in the reactors easier.

The medium employed in the fermentation process in each reactor was the Caldwell and Bryant medium (D. R. Caldwell and M. P. Bryant *Appl. Microb.*, Vol. 14, pp. 794–801 (1966)). The Caldwell and Bryant medium attempts to closely simulate rumen conditions such that rumen bacteria can grow with sufficient nutrients and at optimal conditions. All the chemicals used to make the Caldwell and Bryant medium were purchased from Aldrich (Milwaukee, Wis.) except the cyanocobalamin which was purchased from Fisher Scientific (Pittsburgh, Pa.). The Caldwell and Bryant medium was modified by adding volatile fatty acids to the reactors, except for reactor Al which was the control, in a ratio commonly observed with in vitro fermentations. The modified Caldwell and Bryant medium contained about 68.0 wt. % of acetic acid, about 17.5 wt. % of propionic acid and about 14.5 wt. % of butyric acid. Also, since a carbohydrate, i.e., rye grass, was included as the substrate or biomass, all carbohydrate sources were deleted from the medium. No agar was included in the medium and the medium was not autoclaved. The medium was also neutralized to a pH of about 6.7 with a solution of about 25 wt. % sodium hydroxide to provide an environment more suitable to microbial growth and activity. To suppress methane production during fermentation, the sodium salt of a 0.001 M solution of 2-bromoethanesulfonic acid was added to the medium.

The six reactors employed in the fermentation process were one-liter Pyrex (Corning Glass Works, Corning, N.Y.) Brezelius beakers without pour spouts. Each one-liter beaker was covered with a number 15 EPDM rubber stopper with holes for inserting anaerobic gas tubes and an inverted ground glass sample port.

Nitrogen gas was pumped into each reactor to help maintain an anaerobic environment. Due to the large number of fittings and seals in the fermentor consisting of several reactors the gas system was designed to maintain a slight positive water pressure (about 6 to about 12 inches of water). The positive pressure was intended to prevent air from entering through leaks that might develop and go unnoticed. There was still a chemical potential gradient through the tubing and other materials such that the positive pressure did not prevent diffusion through such materials.

The anaerobic gas purification system was operated at about 3–5 psig. The anaerobic nitrogen was distributed to each reactor through a distribution system of tubing made of Marprene brand norprene (Watson-Marlow, Wilmington, Mass.). Such norprene tubing has a low oxygen permeability and is flexible enough to be used as a general-purpose tubing for gas interconnections in most fermentation apparatus. The anaerobic gas supply was distributed to the individual reactors within the fermentor by aquarium-type gang valves (Whisper, Post Oak Mall, College Station, Tex.) that allowed individual flow regulation.

The exhaust gases from the individual reactors were routed through Marprene tubing through additional gang valves to a backpressure apparatus (water manometer). The gang valves allowed positive-pressure gas supply and exhaust to be applied to and stopped from each reactor without disturbing the other reactors in the fermentor.

All the reactors were then placed in a New Brunswick temperature controlled fermentor equipped with an orbital shaker plate. An Omega model CN76020 feedback temperature controller (Omega International Corp., Stanford, Conn.) was used to control the temperature of the fermentor.

Fermentation in each of the reactors was carried out to completion. Biomass analysis was performed by washing the reactor contents with distilled water into a one-liter Bodum coffee maker (Coffee Beanery, Post Oak Mall, College Station, Tex.). The coffee maker had a about 100 mesh screen fitted to a plunger that was pressed down to force biomass to the bottom of the vessel while allowing the liquid to flow through the screen. The wash was repeated three to four times until the wash water ran clear. The biomass was desiccated in a 105 degree C. oven and weighed. The dry weight following fermentation was compared to the initial substrate dry weight to determine the amount of biomass digested.

Table 1 shows the amount of biomass digested in each reactor over a period of 500 hours. The inhibitory effect of high levels of volatile fatty acids and their salts can be observed in reactors A4–A6 where the initial volatile fatty acid levels were comparatively high in contrast to reactors A1–A3 which were comparatively low. Thus, the higher the initial fatty acid concentration, the lower the digestion of biomass.

TABLE 1

| Reactor | Substrate Concentration (g/L) | Total Reaction Volume (mL) | Inoculum (Rumen Fluid) (mL) | pH | Initial VFA[a] Concentration (g/L) | Conversion % |
|---|---|---|---|---|---|---|
| A1 | 10 | 500 | 100 | 6.7 | 2.193 | 82.8 |
| A2 | 10 | 500 | 100 | 6.7 | 6.931 | 77.7 |
| A3 | 10 | 500 | 100 | 6.7 | 12.465 | 78.5 |
| A4 | 10 | 500 | 100 | 6.7 | 25.743 | 54.8 |
| A5 | 10 | 500 | 100 | 6.7 | 32.039 | 46.9 |
| A6 | 10 | 500 | 100 | 6.7 | 48.316 | 31.8 |

[a]volatile fatty acid in g of acid/L

EXAMPLE 2

Performing volatile fatty acid fermentation by using a biomass pretreatment with alkali improves digestion rates.

Twelve one-liter Pyrex reactors were employed. Reactors S7–S12 contained rye grass which were boiled with 0.1 grams of calcium hydroxide per dry gram of biomass for one hour to make digestion in the reactors easier. The pretreatment was performed over a blanket of anaerobic nitrogen. Following the treatment of the rye grass in reactors S7–S12, the reactors were neutralized to a pH of about 6.7 by carbon dioxide bubbling. The Caldwell and Bryant nutrient package was then added to all twelve reactors. The reactors were allowed 4 hours in the fermentor at 39 degrees C. under positive anaerobic-nitrogen pressure to reach steady-state temperature. The fermentation apparatus was the same type of apparatus employed in Example 1. Fermentation was allowed to go to completion.

After fermentation, the remaining biomass from each reactor was weighed and analyzed as in Example 1. Table 2 discloses that the reactors having the pretreated biomass have a higher conversion of biomass to digested biomass than reactors with the untreated biomass.

TABLE 2

| Reactor | Substrate Concentration (g/L) | Total Reaction Volume (mL) | Inoculum (Rumen Fluid) (mL) | pH | Pretreatment | Conversion % |
|---|---|---|---|---|---|---|
| S1 | 2.5 | 500 | 100 | 6.7 | No | 70.8 |
| S2 | 5.0 | 500 | 100 | 6.7 | No | 66.6 |
| S3 | 10.0 | 500 | 100 | 6.7 | No | 70.8 |
| S4 | 25.0 | 500 | 100 | 6.7 | No | 66.7 |
| S5 | 50.0 | 500 | 100 | 6.7 | No | 54.2 |
| S6 | 75.0 | 500 | 100 | 6.7 | No | 41.6 |
| S7 | 2.5 | 500 | 100 | 6.7 | Yes | 87.7 |
| S8 | 5.0 | 500 | 100 | 6.7 | Yes | 89.4 |
| S9 | 10.0 | 500 | 100 | 6.7 | Yes | 89.0 |
| S10 | 25.0 | 500 | 100 | 6.7 | Yes | 80.8 |
| S11 | 50.0 | 500 | 100 | 6.7 | Yes | 56.8 |
| S12 | 75.0 | 500 | 100 | 6.7 | Yes | 44.4 |

EXAMPLE 3

The effect of high volatile fatty acid concentration on conversion was observed in Example 1 above, and Example 2 above showed that high conversions can be reached at low volatile fatty acid concentrations and low substrate concentrations. Such phenomena are the basis for the continuous countercurrent volatile fatty acid fermentation process of the present example. In one reactor, high conversion and high acids and salts concentrations can not be achieved simultaneously at a given residence time. By arranging more than one reactor in a countercurrent cascade, both objectives can be achieved.

Four modified Bodum coffee makers (Coffee Beanery, Post Oak Mall, College Station, Tex.) were modified to serve as reactors. Each vessel was altered by cutting about ½" off of the top. The rim of each vessel was cut to remove the pour spout allowing good seal against the stopper. The screen was arranged such that it could be moved to separate biomass from liquid. The liquid withdrawal tube was fastened to the screen by a nylon zip-tie.

A V-shaped cut was made in the coffee maker screen. The resulting flap of screen acted as a check valve allowing easier screen withdrawal. The flap sealed against the perforated screen support plate to provide good separation of solids and liquid. Each reactor was stoppered with a #15 stopper and each stopper had an entrance and exit port drilled into it for feeding biomass into and out of the reactor. The four reactors were arranged in series with reactor four as the reactor where fresh biomass was added to the fermentation system. The fermentation process was carried out in the same type of fermentor as described in Example 1 above.

The biomass was ground rye grass and a bagasse/alfalfa blend which had been pretreated with about a 0.1 gm calcium hydroxide/gm of biomass. Initially, Caldwell and Bryant medium as described in Example 1 above was used in the reactors along with the addition of 1 g/L of glucose as a starter carbohydrate.

The reaction system was started with about 50 g/L of pretreated rye grass, the Caldwell and Bryant medium and an eight-day total residence time. Initially, the reactors were agitated by an orbital shaker at about 100 rpm. After 1102 hours, an intervalometer was installed and the shaker was set for 10 minutes on-duration and 50 minutes off-duration.

After about 3697 hours, a double-nutrient version of the Caldwell and Bryant medium was added to the countercurrent system to replenish essential nutrients to continue to help sustain microbial growth and activity. The continuous countercurrent fermentation system received additional inoculations of microbes at 4795 and 5350 hours to replenish the aging colonies in the system. Table 3 summarizes schedule changes made to the experimental design.

Tables 4–7 disclose the amounts of acids and acid salts, represented as gm of acid/L of product, produced in each of the four reactors (reactor 1 being the lowest initial acid-concentration reactor) at specific time periods during the fermentation process. At time 9045.3 hours, reactor 1 produced 6.284 g/L of acid, reactor 2 produced 8.93 g/L of acid, reactor 3 produced 14.897 g/L of acid and reactor 4 produced 23.383 g/L of acid. Thus, unlike the single reactor fermentation process of Example 1 above, the method of the present invention provides for high organic acid production in a reactor of high initial acid concentrations. Also, the method of the present invention showed overall conversion of biomass of greater than about 40 wt. % and acid product concentrations of greater than about 40 g/L before the fermentation process was terminated.

TABLE 3

| Time (h) | Change |
|---|---|
| 0 | 50 g/L pretreated rye grass, 8 day residence time |
| 355 | 100 g/L pretreated rye grass substrate |
| 628 | 12 day residence time |
| 1102 | Began cell and suspended solids recycle |
|  | Began intermittent agitation |
| 1563 | Began recycling wash-water solids |
| 1919 | 100 g/L bagasse and alfalfa |
|  | (100 g pretreated bagasse to 15 g untreated alfalfa) |
| 3620 | 200 g/L bagasse and alfalfa substrate |
| 3697 | Began using double-nutrient package |

TABLE 3-continued

| Time (h) | Change |
|---|---|
| 4795 | Reinoculated with commercial compost bacteria, mixes A, B and C (Decotec, Inc., Portland, OR) |
| 5350 | Reinoculated with commercial compost, swamp, natural anaerobic compost and soil bacteria |
| 7487 | Began 24 day solids residence time and 12 day liquid residence time |
| 8758 | Began 36 day solids residence time and 12 day liquid residence time (1 year anniversary) |

TABLE 4

Reactor 1

Amount[a] of Acids

| Time (h) | Acetic | Propionic | Butyric | Valeric | Total[b] |
|---|---|---|---|---|---|
| 0.0 | 1.305 | 0.234 | 0.000 | 0.000 | 1.539 |
| 1009.3 | 3.552 | 1.813 | 0.521 | 0.354 | 6.401 |
| 1986.3 | 4.489 | 2.638 | 0.720 | 1.255 | 9.517 |
| 3041.6 | 3.273 | 0.929 | 0.237 | 0.431 | 5.925 |
| 4011.1 | 5.312 | 1.676 | 0.654 | 0.390 | 8.519 |
| 5350.3 | 7.700 | 2.553 | 1.123 | 0.631 | 12.422 |
| 6187.6 | 16.717 | 2.354 | 1.751 | 0.733 | 21.970 |
| 7083.9 | 9.081 | 2.750 | 1.268 | 0.516 | 14.122 |
| 8018.8 | 4.105 | 1.593 | 0.304 | 0.126 | 6.194 |
| 9045.3 | 4.391 | 1.590 | 0.234 | 0.069 | 6.284 |

[a]All data are reported as g of acid/L
[b]Includes other organic acids

TABLE 5

Reactor 2

Amount[a] of Acids

| Time (h) | Acetic | Propionic | Butyric | Valeric | Total[b] |
|---|---|---|---|---|---|
| 0.0 | 1.487 | 0.396 | 0.127 | 0.000 | 2.010 |
| 1009.3 | 5.081 | 2.191 | 0.896 | 0.932 | 9.516 |
| 1986.3 | 7.427 | 4.496 | 1.459 | 2.308 | 16.539 |
| 3041.6 | 5.236 | 2.046 | 0.524 | 0.797 | 9.553 |
| 4011.1 | 4.948 | 1.959 | 0.927 | 0.600 | 8.909 |
| 5350.3 | 10.234 | 3.223 | 0.872 | 0.768 | 16.262 |
| 6187.6 | 17.071 | 2.854 | 2.241 | 1.215 | 24.743 |
| 7083.9 | 16.198 | 3.839 | 2.445 | 0.950 | 24.462 |
| 8018.8 | 6.908 | 2.998 | 0.694 | 0.368 | 11.226 |
| 9045.3 | 6.141 | 2.265 | 0.373 | 0.154 | 8.933 |

[a]All data are reported as g of acid/L
[b]Includes other organic acids

TABLE 6

Reactor 3

Amount[a] of Acids

| Time (h) | Acetic | Propionic | Butyric | Valeric | Total[b] |
|---|---|---|---|---|---|
| 0.0 | 2.452 | 0.917 | 0.242 | 0.000 | 3.611 |
| 1009.3 | 6.643 | 2.143 | 1.531 | 1.095 | 12.050 |
| 1986.3 | 7.627 | 3.957 | 1.295 | 2.051 | 16.171 |
| 3041.6 | 7.686 | 3.311 | 0.986 | 1.165 | 13.958 |
| 4011.1 | 9.150 | 3.494 | 1.237 | 0.768 | 15.205 |
| 5350.3 | 14.034 | 4.700 | 1.750 | 1.192 | 22.415 |
| 6187.6 | 22.640 | 4.334 | 3.932 | 1.832 | 34.910 |
| 7083.9 | 18.597 | 4.718 | 3.008 | 1.209 | 28.748 |

TABLE 6-continued

Reactor 3

| | Amount[a] of Acids | | | | |
|---|---|---|---|---|---|
| Time (h) | Acetic | Propionic | Butyric | Valeric | Total[b] |
| 8018.8 | 10.209 | 4.356 | 1.269 | 0.690 | 17.015 |
| 9045.3 | 9.600 | 4.080 | 0.744 | 0.375 | 14.897 |

[a]All data are reported as g of acid/L
[b]Includes other acids

TABLE 7

Reactor 4

| | Amount[a] of Acids | | | | |
|---|---|---|---|---|---|
| Time (h) | Acetic | Propionic | Butyric | Valeric | Total[b] |
| 0.0 | 2.741 | 0.633 | 0.272 | 0.366 | 4.138 |
| 1009.3 | 12.174 | 1.474 | 2.258 | 1.428 | 18.232 |
| 1986.3 | 12.637 | 6.655 | 2.194 | 3.247 | 26.116 |
| 3041.6 | 9.584 | 4.120 | 1.192 | 1.326 | 17.015 |
| 4011.1 | 12.614 | 4.871 | 1.785 | 1.565 | 21.567 |
| 5350.3 | 10.672 | 1.445 | 1.524 | 0.361 | 15.509 |
| 6187.6 | 22.708 | 3.781 | 4.469 | 2.281 | 36.478 |
| 7083.9 | 23.596 | 5.398 | 4.286 | 1.735 | 36.669 |
| 8018.8 | 16.163 | 6.876 | 2.129 | 1.174 | 27.017 |
| 9045.3 | 14.534 | 6.580 | 1.384 | 0.713 | 23.383 |

[a]All data are reported as g of acid/L
[b]Includes other acids

What is claimed is:

1. An apparatus for producing organic acids and salts of organic acids by anaerobic fermentation of biomass comprising:
   a first container means and a second container means for containing the biomass,
   a first means for transporting biomass into said first container means,
   a second means for transporting biomass from said first to said second container means,
   a means for removing biomass from said second container means, and
   a means for washing the organic acids and the salts of the organic acids from the biomass, said means comprising a first means to direct water into counter current contact with biomass from said second container means to produce an organic acids and salts of organic acids containing water stream and a second means to direct said organic acids and salts of organic acids containing water stream into counter current contact with biomass from said first container means.

2. The apparatus of claim 1, wherein the first and second container means each comprises a core imbedded in earth with supporting berms, said core provided with sides to prevent leakage from said core.

3. The apparatus of claim 2, wherein said sides comprise a water barrier comprising clay, a porous layer comprising gravel and a lining comprising rubber or polyvinyl chloride.

4. The apparatus of claim 3, wherein the first and second container means each further comprises a standpipe in communication with the porous layer.

5. The apparatus of claim 2, wherein the means for removing biomass from said second container means opens adjacent a bottom of said second container means.

6. The apparatus of claim 1, wherein said first and second directing means each comprises a hollow column having baffles to prevent channeling of liquid through the biomass.

7. The apparatus of claim 1, further comprising a means for evenly distributing the biomass in said first and said second container means.

8. The apparatus of claim 7, wherein the means for evenly distributing the biomass comprises motorized fans or slingers.

9. An apparatus for producing organic acids and salts of organic acids by anaerobic fermentation of biomass comprising:
   a first container means and a second container means for containing the biomass,
   a first means for transporting biomass into said first container means,
   a second means for transporting biomass from said first to said second container means,
   a means for removing biomass from said second container means, and
   means for washing the organic acids and the salts of the organic acids from said biomass, said means comprising a means to direct fresh water into contact with biomass from said second container means to produce an organic acids and salts of organic acids containing water stream and means to contact said organic acids and salts of organic acids containing water stream with biomass from said first container means.

* * * * *